United States Patent [19]

Kawaki et al.

[11] Patent Number: 5,034,492
[45] Date of Patent: Jul. 23, 1991

[54] SULFUR-CONTAINING AROMATIC VINYL COMPOUND, CROSSLINKED POLYMER ARTICLES AND LENS

[75] Inventors: Takao Kawaki, Tokyo; Makoto Kobayashi, Nagareyama; Osamu Aoki, Matsudo; Tatsuo Iwai, Tokyo; Yukifumi Goto, Kashiwa, all of Japan

[73] Assignee: Mitsubishi Gas Chemical Company, Inc., Tokyo, Japan

[21] Appl. No.: 530,448

[22] Filed: Jun. 1, 1990

Related U.S. Application Data

[62] Division of Ser. No. 306,307, Feb. 3, 1989, abandoned.

[30] Foreign Application Priority Data

Feb. 3, 1988 [JP] Japan ................................ 63-21890
Mar. 9, 1988 [JP] Japan ................................ 63-53793

[51] Int. Cl.⁵ .............................................. C08G 18/67
[52] U.S. Cl. .................................... 528/75; 350/409; 568/55
[58] Field of Search ................. 528/75; 350/409; 568/55

[56] References Cited

U.S. PATENT DOCUMENTS

| | | | |
|---|---|---|---|
| 2,780,567 | 2/1957 | Kine et al. | 568/55 |
| 2,858,297 | 10/1958 | Melamed | 528/75 |
| 2,879,250 | 3/1959 | Eisenmann et al. | 528/75 |
| 3,062,892 | 11/1962 | Schneider | 568/55 |
| 3,078,259 | 2/1963 | Hatch et al. | 568/55 |

FOREIGN PATENT DOCUMENTS 2032135 2/1969 France.
386934 6/1973 U.S.S.R..

*Primary Examiner*—John Kight, III
*Assistant Examiner*—Rabon Sergent
*Attorney, Agent, or Firm*—Wenderoth, Lind & Ponack

[57] ABSTRACT

A novel sulfur-containing aromatic vinyl compound represented by the following general formula (I)

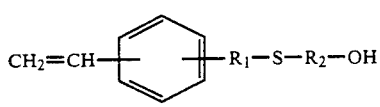

wherein $R_1$ represents an alkylene group having 1 to 3 carbon atoms and $R_2$ represents an alkylene group having 2 to 8 carbon atoms, and the two bonds in the benzene ring are meta or para to each other. A curable composition comprising at least one of the said vinyl compounds, an isocyanate compound and a radical polymerization initiator. On heating, the composition gives a crosslinked polymer article useful as lenses.

9 Claims, 2 Drawing Sheets

SULFUR-CONTAINING AROMATIC VINYL COMPOUND, CROSSLINKED POLYMER ARTICLES AND LENS

This application is a division of now abandoned application, Ser. No. 07/306,307 filed on Feb. 3, 1989.

This a novel sulfur-containing aromatic vinyl compound, a composition comprising it, a crosslinked polymer article obtained by using the compound as a main monomer, and to a lens of the crosslinked polymer. Particularly, it pertains to a novel sulfur-containing aromatic vinyl compound capable of giving a cured product having a high refractive index by cast polymerization, and its use.

Organic polymers used for optical lenses include, for example, poly(methyl methacrylate), poly(diethylene glycol bisallyl carbonate), polystyrene and polycarbonate.

Poly(methyl methacrylate) and poly(diethylene glycol bisallyl carbonate) have predominantly been used as lenses for sight correction eyeglasses.

Lenses composed of poly(methyl methacrylate) or poly(diethylene glycol bisallyl carbonate) have a refractive index of as low as about 1.5. To obtain sight correction lenses from such polymers, the thickness of these lenses at their peripheral ends becomes larger than that of an inorganic glass lens.

The demand for weight and thickness reduction has been raised by consumers who need eyeglasses, and to meet this demand, it has been desired to develop transparent organic polymers having a high refractive index.

To develop organic polymers having a high refractive index, various polymers have been proposed as shown below.

(1) U.S. Pat. No. 4,369,298

This patent describes a "cured resin consisting substantially of a first polymer unit derived from a unsaturated compound having two terminal vinyl groups consisting of bis(alkyleneoxyphenyl)diacrylates or dimethacrylates, bis(alkyleneoxyphenyl)diallyl ethers and bis-(alkyleneoxyphenyl)diallyl carbonates, and a second polymer unit derived from another unsaturated compound radical-polymerizable with the first-mentioned unsaturated compound, said polymer units being bonded to each other at random." This patent document also states: "The aforesaid cured resin can be produced by copolymerizing an intimate mixture consisting substantially of at least one compound selected from the first-mentioned unsaturated compounds having two terminal vinyl groups and prepolymers thereof and at least one compound selected from other unsaturated compounds radicalcopolymerizable with the first-mentioned unsaturated compounds and prepolymers thereof in the presence of a radical polymerization initiator. A lens composed of the aforesaid cured resin has a high refractive index, excellent transparency and excellent fire retardancy."

(2) Japanese Laid-Open Patent Publication No. 133211/1984

This patent document states that by reacting a composition composed of the following components A, B and C, a resin having a high refractive index, transparency and antishock properties suitable for plastic lenses can be produced.

A. At least one hydroxyl group-containing vinyl monomer selected from the following (I), (II) and (III).

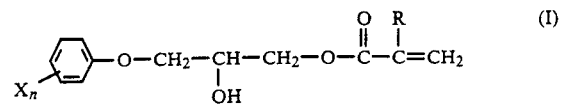

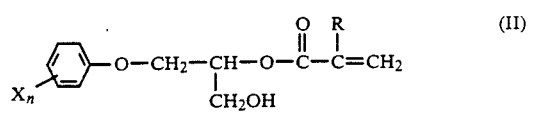

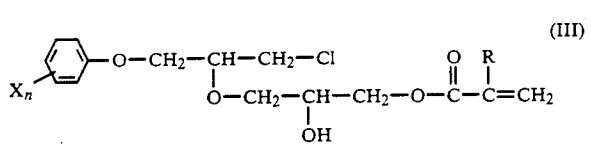

wherein X represents bromine or iodine, R represents a methyl group or a hydrogen atom, and n represents an integer of 1 to 5, B. an isocyanate compound with two or more functional groups, and C. a vinyl monomer.

(3) Japanese Laid-Open Patent Publication No. 11513/1985

This patent document describes a resin composed of a polymer of a composition composed of (A) a mixture or an addition reaction product of (i) an isocyanate compound with two or more functional groups and (ii) a hydroxyl group-containing vinyl monomer of the following formula (I) or (II)

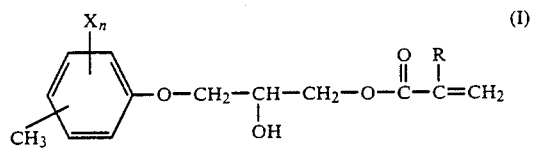

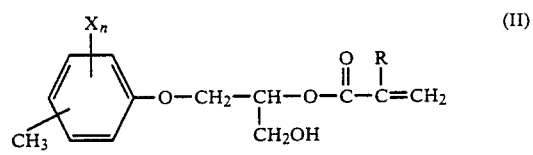

wherein X represents bromine or iodine, R represents a methyl group or a hydrogen atom, and n represents an integer of 1 to 4, and (B) a vinyl monomer, and this resin has a high refractive index, transparency and antishock property suitable for plastic lenses.

(4) Japanese Laid-Open Patent Publication No. 51706/1985

This patent document describes a resin obtained by reacting a (meth)acrylate of the following general formula

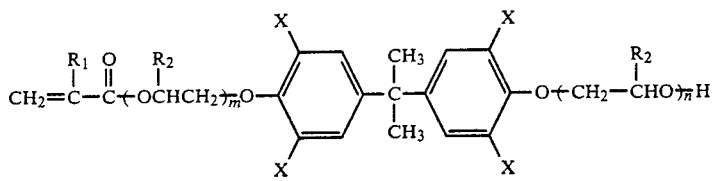

wherein $R_1$ and $R_2$ represent a hydrogen atom or a methyl group, m and n are integers and a total of these is 0 to 4, and x represents chlorine, iodine or bromine, wherein $R_1$ represents a hydrogen atom or a methyl group, and $R_2$ represents either one of the following groups

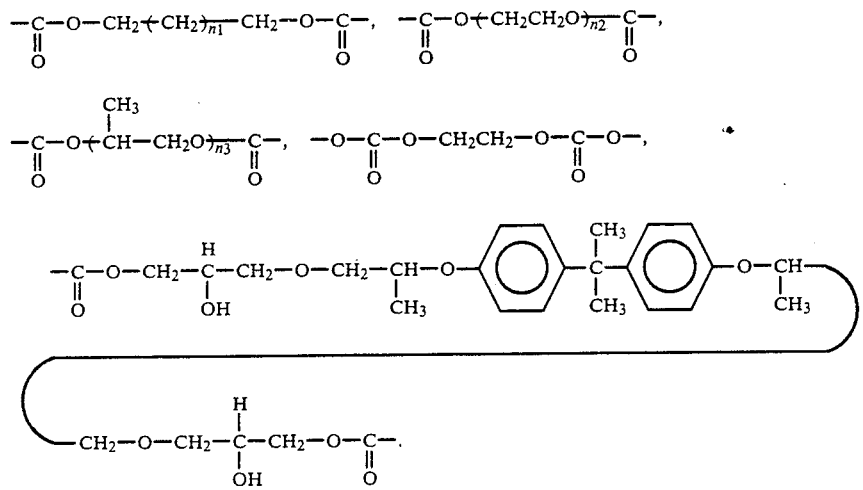

and vinyl-polymerizing the resulting urethane (meth)acrylate. It describes that the resin has a high refractive index suitable for plastic lenses.

(5) Japanese Laid-Open Patent Publication No. 164615/1983

This patent document describes a polyurethane resin for plastic lenses which is obtained by reacting a polyol having a halogen content of at least 30% by weight (for example, dibromoneopentyl glycol or tetrabromobisphenol A) with a polyisocyanate such as xylylene diisocyanate or isophorone diisocyanate in an NCO/OH mole ratio of from 0.5 to 1.5.

(6) Japanese Laid-Open Patent Publication No. 104901/1982

This patent document describes a synthetic resin lens obtained by radical polymerization of a monomeric mixture composed of 10 to 30 % of a monomer represented by the following formula [I], 1 to 15 % of a monomer represented by the following formula [II] and 55 to 89 % of a radical-polymerizable monomer.

$n_1$ represents an integer of 6 to 20, $n_2$ represents an integer of 3 to 20, and $n_3$ represents an integer of 3 to 20.

(7) Japanese Laid-Open Patent Publication No. 217229/1985

This patent document describes a sulfur-containing polyurethane resin for lenses which is obtained by reacting a sulfur-containing polyol having a sulfur content of at least 20 % by weight and a polyisocyanate at an NCO/OH mole ratio of from 0.5 to 1.5. It specifically shows $HOCH_2,CH_2SCH_2CH_2OH$, $HOCH_2CH_2SCH_2SCH_2CH_2OH$, and $HOCH_2CH_2SSCH_2CH_2OH$ as the sulfur-containing polyol.

These resins described in the prior art have considerably improved refractive indices for use as plastic lenses of eyeglasses. However, since the resins described in the above-cited references (1) to (6) are obtained by using monomers of a specific structure containing a halogen such as bromine, lenses produced from these resins cost high and have unsatisfactory weather-ability. Another defect is that they have a specific gravity of about 1.4. The resin described in reference (7) suffers less from these defects because it does not use a halogen-containing monomer, but it has low thermal resistance.

It is an object of this invention to provide a novel sulfur-containing aromatic vinyl compound as a mono-

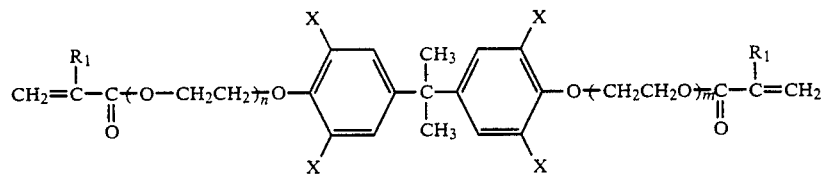

[I]

wherein $R_1$ represents a hydrogen atom or a methyl group, X represents a halogen atom other than fluorine, and n+m represents an integer of 0 to 8.

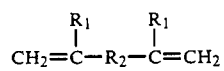

[II]

mer capable of giving a polymer having excellent properties for use as plastic eyeglass lens.

Another object of this invention is to provide a polymer article suitable as a plastic lens having a high refractive index.

Still another object of this invention is to provide a curable composition capable of giving the aforesaid polymer article.

Yet another object of this invention is to provide an industrially advantageous process for production of the aforesaid polymer article.

A further object of this invention is to provide a transparent plastic lens having a high refractive index, high heat resistance and a relatively low specific gravity.

Additional objects of this invention will become apparent from the following description.

According to this invention, the above objects of this invention are achieved by a sulfur-containing aromatic vinyl compound represented by the following general formula [I]

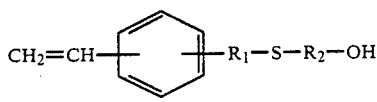

wherein $R_1$ represents an alkylene group having 1 to 3 carbon atoms and $R_2$ represents an alkylene group having 2 to 8 carbon atoms, and the two bonds in the benzene ring are meta or para to each other; and a crosslinked polymer article obtained by bulk polymerization of at least one sulfur-containing aromatic vinyl compound of general formula I) above as a main monomer.

The present invention will now be described below in detail.

Sulfur-containing Aromatic Vinyl Compound [I] and Process for Production Thereof The sulfur-containing aromatic vinyl compound of this invention is represented by general formula [I].

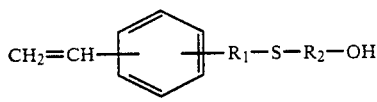

In general formula [I], $R_1$ represents an alkylene group having 1 to 3 carbon atoms. Specific examples are

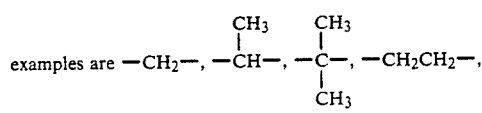

—CH$_2$CH$_2$CH$_2$—, and —CH$_2$— is especially preferred.

$R_2$ represents an alkylene group having 2 to 8, preferably 2 to 6, carbon atoms. Specific examples are —CH$_2$—CH$_2$—, —CH$_2$CH$_2$CH$_2$—,

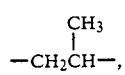

—CH$_2$CH$_2$CH$_2$CH$_2$—, $$-CH_2CHCH_2-, \quad -CH_2CH_2CH-,$$
$$\hspace{1em}|\hspace{6em}|$$
$$CH_3 \hspace{5em} CH_3$$

—CH$_2$CH$_2$CH$_2$CH$_2$CH$_2$— and
—CH$_2$CH$_2$CH$_2$CH$_2$CH$_2$CH$_2$—. Preferred are
—CH$_2$CH$_2$—, —CH$_2$CH$_2$CH$_2$— and

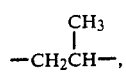

and —CH$_2$CH$_2$— is especially preferred.

In general formula [I], the two groups bonded to the benzene ring may be meta or para to each other.

Preferred specific examples of the sulfurcontaining aromatic vinyl compounds of general formula [I] are metal or para-substitution products of the following compounds.

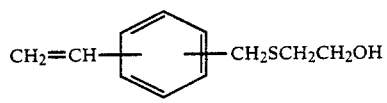

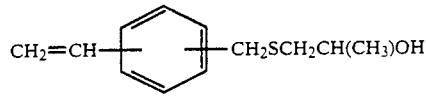

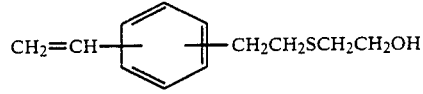

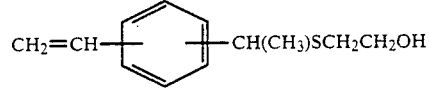

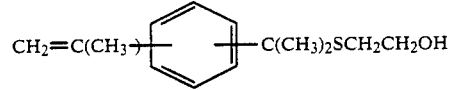

Of these, 2-(3-vinylbenzylthio)ethanol, 2-(4-vinylbenzythio)ethanol and a mixture of these are especially preferred.

The sulfur-containing aromatic vinyl compound of formula [I] provided by this invention can generally be produced by reacting a halogenated styrene derivative represented by the following general formula [II]

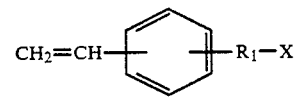

wherein $R_1$ represents an alkylene group having 1 to 3 carbon atoms, and X represents chlorine or bromine, and the two bonds in the benzene ring are meta or para to each other, with a hydroxyl-containing thiol compound represented by the following general formula [III]

$$HO-R_2-SH\ldots \hspace{4em} (8\ III)$$

wherein $R_2$ represents an alkylene group having 2 to 8 carbon atoms, in the presence of an alkali.

Examples of the halogenated styrene derivative of general formula [II] include chloromethylstyrene, bromomethylstyrene, chloroethylstyrene and bromoethylstyrene, including both meta- and para-forms.

Examples of the hydroxyl-containing thiol compound of general formula [III] include 2-mercaptoethanol, 3-mercaptopropanol, 2-mercapto-1-methylethanol and 6-mercaptohexanol The alkali used in the reaction between the compounds of formulae [II] and [III] acts to scavenge the by-product hydrogen halide formed as a result of the reaction. It may be a compound which reacts with the hydrogen halide to form the corresponding alkali halide. Preferably, it may be an inorganic base such as sodium hydroxide, potassium hydroxide, sodium carbonate, potassium carbonate and quaternary ammonium hydroxide.

The reaction may be carried out by stirring 1 mole of the halogenated styrene derivative II), about 1 to about 2 moles, preferably about 1 to about 1.5 moles, of the hydroxyl-containing thiol compound III) and about 1 to about 2 moles of the alkali without a solvent or in an inert solvent at a temperature ranging from about 0° C. to the boiling point of the reaction mixture for several minutes to 24 hours.

The inert solvent which may be used in this reaction may be, for example, water, an alcohol such as methanol or ethanol, an ether such as tetrahydrofuran or dioxane, a ketone such as acetone or methyl ethyl ketone, or an aromatic hydrocarbon such as benzene or toluene.

Since heat is generated as the reaction proceeds, the reaction temperature can be easily controlled by gradually adding one of the halogenated styrene derivative [III], the hydroxyl-containing thiol compound [III], and the alkali.

After the reaction, the resulting salt and the unreacted alkali are removed by such means as filtration or washing with water. Then, the solvent, the unreacted halogenated styrene derivative and hydroxyl-containing thiol compound [III] were evaporated by heating under reduced pressure to give the desired sulfur-containing aromatic vinyl compound [I]. If required, it can be purified to a higher degree by distilling it under reduced pressure, or passing it through a column filled with activated carbon or silica.

When the above reaction, separation and purification steps involve heating, it is desirable to add a known radical polymerization inhibitor and thereby to prevent polymerization of the sulfur-containing vinyl compound [I].

The sulfur-containin9 aromatic vinyl compound [I] in which $R_1$ has 2 carbon atoms may be synthesized by an alternative method which comprises addition-reaction between divinylbenzene and the hydroxyl-containing thiol compound of general formula [III].

Curable Composition and Preparation Thereof

There are roughly the following two curable compositions which can be prepared in accordance with this invention using the sulfur-containing aromatic vinyl compound [I].

[A-1]

A curable composition comprising the sulfurcontaining aromatic vinyl compound of formula [I], an isocyanate compound and a radical polymerization initiator.

[A-2]

A curable composition comprising the sulfurcontaining aromatic vinyl compound of formula [I], another radical-polymerizable vinyl monomer, an isocyanate compound and a radical polymerization initiator.

The curable composition [A-2] differs from the curable composition [A-1)] in that it further includes the other radical polymerizable vinyl monomer. In the following description, the sulfur-containing aromatic vinyl compound and the isocyanate compound may sometimes be referred to as the "main monomer", and the other radical polymerizable vinyl monomer, as the "comonomer".

The proportions of the main mohomer [I] and the comonomer in the composition [A-2] are determined depending upon the type of the main monomer, the type of the comonomer, the properties and use of the desired crosslinked polymer to be obtained, and economy. It is advantageous to use a composition containing 100 to 60 % by weight, preferably 100 to 70 % by weight, of the main monomer and 0 to 40 % by weight, preferably 0 to 30 % by weight, of the comonomer.

The comonomer is a radical-polymerizable monomer containing an ethylenic bond which copolymerizes in bulk with the main monomer of general formula I and the isocyanate compound to give a crosslinked polymer, preferably a vinyl compound, an acrylic compound or an allyl compound.

Specific examples of the comonomer are vinyl compounds such as styrene, chlorostyrene and divinylbenzene, acrylic compounds such as methyl (meth)acrylate, dicyclopentenyl (meth)acrylate, cyclohexyl (meth)acrylate, phenyl (meth)acrylate, benzyl (meth)acrylate and chlorophenyl (meth)acrylate, and allyl compounds such as diallyl phthalate and diethylene glycol bisallyl carbonate. Preferred among these comonomers are styrene, chlorostyrene, divinylbenzene, phenyl (meth)acrylate, benzyl (meth)acrylate and diallyl phthalate.

The isocyanate compound used in the curable compositions [A-1] and [A-2] may be an aliphatic, alicyclic or aromatic isocyanate. Aromatic isocyanates are preferred. Preferably, the isocyanate compound is difunctional or higher.

Specific examples of the isocyanate compound include isophorone diisocyanate, hexamethylene diisocyanate, 2-isocyanatoethyl methacrylate, phenyl isocyanate, 4-vinylbenzyl isocyanate, m- or p-xylylene diisocyanate, tolylene diisocyanate, phenylene diisocyanate, 4,4'-diphenylmethane diisocyanate, isopropylidenebis(4-phenyl isocyanate), and chlorinated or brominated products of these isocyanates. Aromatic diisocyanates compounds are preferred. Xylylene diisocyanate and tolylene diisocyanate are especially preferred. If desired, two or more of these isocyanates may be used in combination.

The isocyanate compound may be used in such a proportion that the ratio of the total moles of the vinyl group to the total moles of the isocyanate groups is from about 0.5 to about 2, preferably from about 0.7 to about 2.

To control the polymerization reaction and improve the properties of the crosslinked polymer article, a minor proportion of a polyfunctional compound such as trimethylolpropane tris(beta-thioglycollate), trimethylolpropane tris(beta-thiopropionate), pentaerythritol tetrakis-(beta-thioglycollate) and pentaerythritol tetrakis(beta-thiopropionate) may be added to the curable compositions of this invention.

By bulk-polymerizing the curable composition [A-1] or [A-2] in a mold, a crosslinked polymer article can be formed.

A compound which decomposes by the action of heat and/or light to generate radicals is used as the radical polymerization initiator. Compounds generally known as radical polymerization initiators for the polymerization of vinyl compounds and allyl compounds are preferably used in this invention.

Examples of the radical polymerization initiator include azo compounds and peroxides, specifically benzoyl peroxide (BPO), diisopropyl peroxycarbonate, azobisisobutyronitrile, di-t-butyl peroxide, cumene hydroperoxide, $H_2O_2$, potassium persulfate and ammonium persulfate. Curing may also be effected by ultraviolet light using a photosensitizer such as benzophenone, benzoin or benzoin methyl ether. These radical polymerization initiators may be used singly or in combination.

The amount of the radical polymerization initiator is usually 0.01 to 5 parts by weight, preferably 0.1 to 3 parts by weight, per 100 parts by weight of the monomeric mixture.

When the isocyanate compound is used as a monomer component, a catalyst may be added to increase its reactivity and the strength of the resulting crosslinked polymer article. Examples of the catalyst are tin compounds such as dibutyltin dilaurate, dimethyltin dichloride and stannous octoate; compounds of metals such as zinc, lead, aluminum, titanium and vanadium; and Lewis bases such as tertiary amines and tertiary phosphines.

In the preparation of the crosslinked polymer article by this invention, additives which are desired to be incorporated in the resulting polymer should be added in advance to the curable composition. The additives may be those which are generally used as additives to polymers, and include, for example, stabilizers, ultraviolet absorbers, coloration inhibitors, antioxidants, pigments and fire retardants.

Crosslinked polymer article and its production

The crosslinked polymer article in accordance with this invention may be produced by
a) preparing a curable composition of the above ingredients,
b) feeding the curable composition into a mold,
c) heating the curable composition in the mold to form a crosslinked polymer article, and then
d) withdrawing the resulting polymer article from the mold.

Thus, according to this invention, the curable composition containing the radical polymerization initiator is fed into the mold, and heated and/or irradiated with ultraviolet light to thereby generate radicals. As a result, the monomeric mixture polymerizes in bulk in the mold and a cured polymer article of a three-dimensional network structure is formed.

The curable composition of this invention may be directly fed into the mold. If desired, prior to it, the composition may be subjected to preliminary polymerization. The preliminary polymerization may be effected by heating the curable composition for a short period of time to an extent such that the composition does not lose flowability. The preliminary polymerization is frequently effective because it can prevent occurrence of raisings and depressions or cracking on the surface of the molded article which is due to an abrupt reaction occurring in the mold.

At room temperature, the curable composition to be fed into the mold usually has flowability and does not start to polymerize. But when the curable composition is fed into the mold, and the mold is heated, or irradiated with ultraviolet light, or heated and simultaneously irradiated with ultraviolet light, the polymerization reaction of the monomeric mixture starts to proceed. Heating the mold is a preferred embodiment of performing the polymerization because the equipment is simple, the polymerization reaction can be easily controlled, and the method is economical.

The temperature at which the mold is heated is in the range of 40° to 130° C., preferably 40 to 120° C. It is not always necessary to heat the mold at a fixed temperature. Investigations of the present inventors have shown that a polymer article having excellent properties as a lens can be obtained by heating the mold such that the polymerization is started at relatively low temperatures within the above-specified range, and the rate of temperature elevation is accelerated as the temperature becomes higher. The heating time is usually at least 1 hour, preferably at least 5 hours. The upper limit of the heating time is 24 hours, preferably 20 hours.

The structure of the mold depends upon the shape of the desired molded article. For example, for preparation of an optical lens, the mold may be of a simple structure composed of two glass sheets and an O-ring interposed between them.

After the polymerization and curing have been completed in the mold, the molded article is withdrawn from the mold. The molded article so withdrawn may be directly used as a product, or submitted to the next step. As required, the molded article may be heattreated for post cure.

Because the crosslinked polymer article obtained by the present invention has a high refractive index and is transparent, it has very good properties for use as a lens for sight-correcting eyeglasses. Furthermore, the resulting molded article shows excellent thermal resistance, impact strength, processability, chemical resistance and dyeability, and therefore, has a very high utilitarian value as an optical lens, as can be seen from examples given below.

Figure 1:
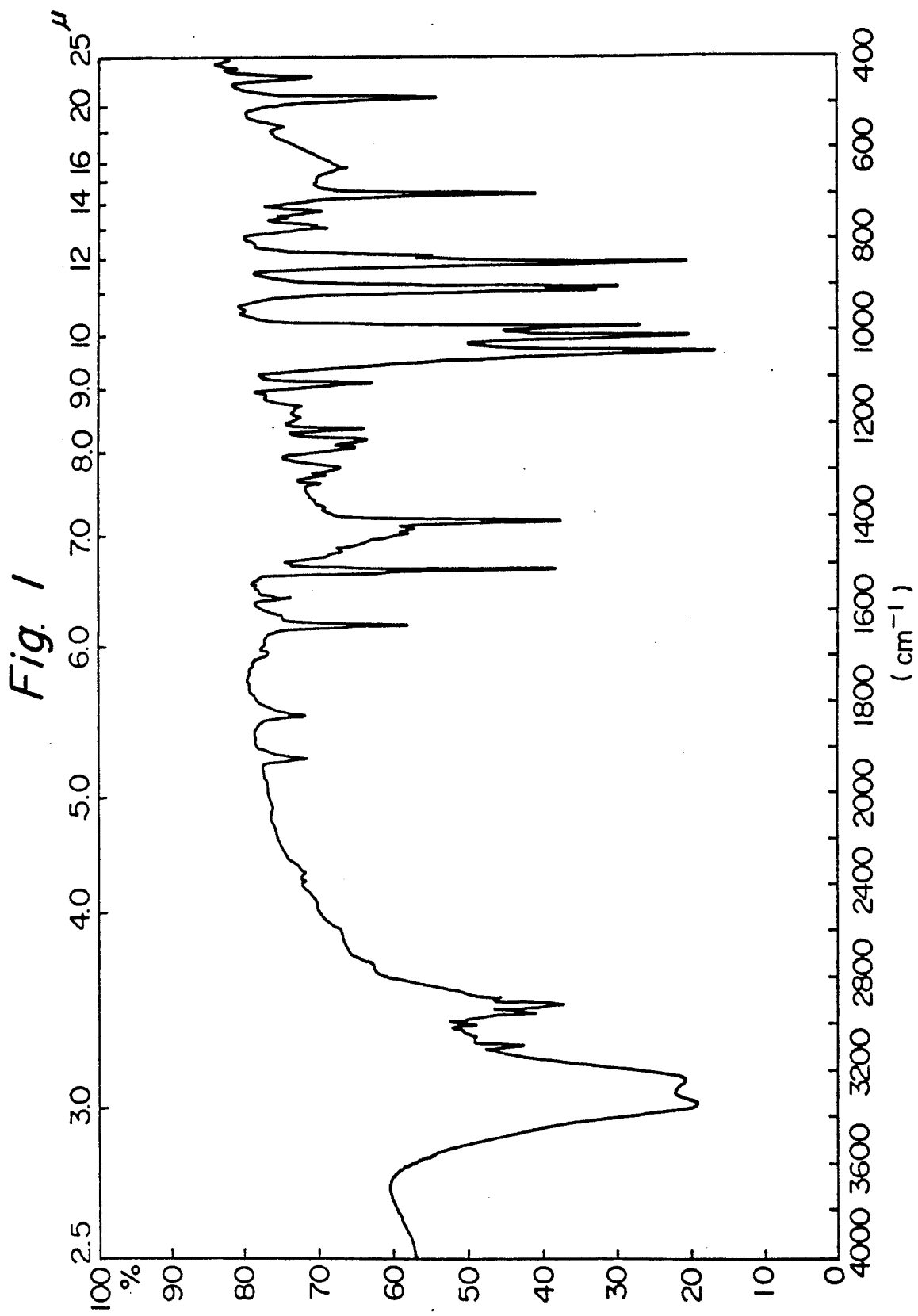
FIGS. 1 and 2 respectively show the infrared absorption spectrum (FIG. 1) and the NMR spectrum (FIG. 2) of 2-(4-vinylbenzylthio)ethanol obtained in Example 3.

The following Examples specifically illustrate the present invention.

The molded articles obtained in these examples were tested for thermal resistance and impact strength by the following methods.

(1) Thermal resistance

The Vicat heat softening temperature of the cured article under a load of 1 kg was measured. When it had a Vicat heat softening temperature of 120° C. or higher, the cured article was regarded as having good thermal resistance.

(2) Impact strength

A disc-shaped sample, 60 mm in diameter and 2.5 mm in thickness, was prepared from the cured article. An iron ball weighing 30 g was let fall onto the sample from a height of 1.2 m. When the sample was not broken, the sample was regarded as having good impact strength.

EXAMPLE 1

A polymerization inhibitor, p-methoxyphenol (1.24 g; 0.01 mole), was added to a mixture of 152 g (1.0 mole) of chloromethylstyrene (m-/p- mixture), 165 g (1.2 moles) of potassium carbonate and 1 liter of methyl ethyl ketone, and the mixture was boiled. 78 g (1.0 mole) of 2-mercaptoethanol was added dropwise over 1 hour. The boiling was continued for 3 hours. After the mixture was cooled to room temperature, the resulting potassium chloride and the unreacted potassium carbonate were separated by filtration, and the solid matter left on the filter was washed with 5ml of methyl ethyl ketone.

The filtrate was concentrated under reduced pressure by an aspirator to remove methyl ethyl ketone. Subsequently, the concentrate was distilled under reduced pressure (140° C./1-2 mmHg) to give 127 9 of a colorless transparent liquid.

Analysis showed that the above liquid is a mixture of 2-(3-vinylbenzylthio)ethanol and 2-(4-vinylbenzylthio)ethanol.

Elemental Analysis C=68.1 %, H=7.14 %, S=16.4 %, O=8.35 % (calculated: C=68.0 %, H=7.22 %, S=16.5 %, 0=8.25 %)

Infrared absorption spectrum 3300 cm$^{-1}$ stretching vibration of —OH 3090 cm$^-$: stretching vibration of C—H of the benzene ring
2900-3000 cm$^{-1}$ stretching vibration of —CH$_2$—
1625 cm$^{-1}$ stretching vibration of CH$_2$=CH—
1500 cm$^{-1}$: vibration of the benzene ring
1010 cm$^{-1}$: stretching vibration of —O—

H$^1$-NMR spectrum 2.0 ppm: H of OH
2.6 ppm: H of CCH$_2$S
3.7 ppm: H of CCH$_2$O
3.74 ppm: H of CH$_2$ adjacent the benzene ring
5.5 ppm: H of =CH$_2$ of the vinyl group
6.6 ppm: H of —CH= of the vinyl group
7.2 ppm: H of the benzene ring

EXAMPLE 2

Seventy-five grams of the mixture of 2-(3-vinylbenzylthio)ethanol and 2-(4-vinylbenzylthio)ethanol obtained in Example 1, 25 g of m-xylylene diisocyanate, 0.2 g of Perbutyl 0 t-butyl peroxy(2-ethylhexanoate)), 0.2 g of Perbutyl A (t-butyl peroxyacetate) and 50 ppm of dibutyltin dilaurate were uniformly mixed. The mixture was poured into a mold composed of two glass sheets and a rubber gasket. The temperature was elevated linearly from 40° C. to 90° C. over 10 hours, and then the mixture was maintained at 90° C. for 2 hours to polymerize and cure it.

The resulting cured article was colorless and transparent and had a refractive index, N$_D^{20°\,C.}$, measured by an Abbe refractometer, of 1.625 and an Abbe number of 33. Thus, it had good optical properties with a high refractive index and a high Abbe number. The cured article had lightweight with a specific gravity of 1.24 and good thermal resistance and impact strength, and was excellent as a lens, particularly as a high refractive lens for eyeglasses.

EXAMPLE 3

A polymerization inhibitor, p-methoxyphenol (1.24 g; 0.01 mole), was added to a mixture of 152 g (1.0 mole) of p-(chloromethyl)styrene, 60 g (1.5 moles) of sodium hydroxide and 0.5 liter of tetrahydrofuran. The resulting mixture was boiled, and 78 g (1.0 mole) of 2-mercaptoethanol was added dropwise over 0.5 hour. The boiling was continued for 3 hours. After cooling to room temperature, the reaction mixture was filtered by the same operation as in Example 1, and distilled under reduced pressure (140-145 ° C./1-2 mmHg) to give 93 g of 2-(4-vinylbenzylthio)ethanol as a white solid.

Purity determined by gas chromatography: 98.0 %

Elemental analysis values C=68.2 %, H=7.34 %, S=16.3 %, O=8.12 % (calculated: C=68.0 %, H=7.22 %. S=16.5 %, O=8.25 %)

Infrared absorption spectrum (see FIG. 1)

3300 cm$^{-1}$: stretching vibration of —OH
1625 cm$^{-1}$ stretching vibration of CH$_2$=CH—
1500 cm$^{-1}$ vibration of the benzene ring
1010 cm$^{-1}$: stretching vibration of —O—

Figure 2:
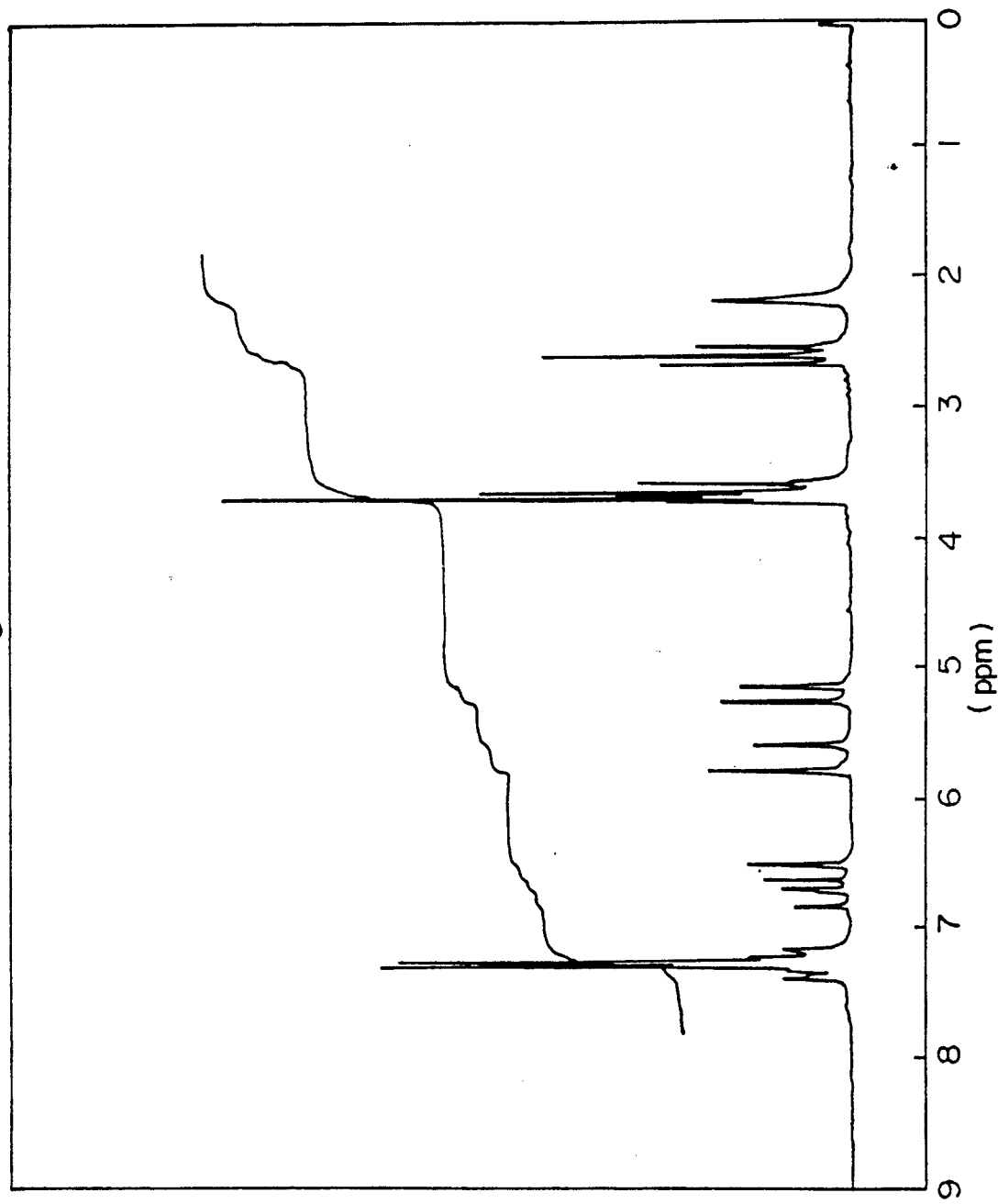

H$^1$—NMR spectrum (see FIG. 2)

2.1 ppm: H of OH
2.6 ppm: H of CCH$_2$S
3.6 ppm: H of CCH$_2$O
3.7 ppm: H of CH$_2$ adjacent the benzene ring
5.4 ppm: H of =CH$_2$ of the vinyl group
6.7 ppm: H of —CH= of the vinyl group 7.3 ppm: H of the benzene ring

EXAMPLE 4

A monomeric mixture composed of 67 g of the mixture of 2-(4-vinylbenzylthio)ethanol and 2-(3-vinylbenzylthio)ethanol obtained in Example 1 and 33 g of m-xylylene diisocyanate was mixed with 0.1 g of Perbutyl O [t-butyl peroxy(2-ethylhexanoate)], 0.1 g of Perbutyl A (t-butyl peroxyacetate) and 100 ppm of dibutyltin dilaurate as polymerization initiators. The mixture was poured into a mold composed of two glass sheets and a rubber gasket. The temperature was elevated linearly from 40° C. to 90° C. over 12 hours, and then the mixture was maintained at 90° C. for 1 hour to polymerize and cure it.

The mole ratio of 2-(vinylbenzylthio)ethanol/(m-xylylene diisocyanate x 2), i.e. the ratio of the total moles of the vinyl group to the total moles of the isocyanate groups, was 1.0.

The resulting cured article was colorless and transparent and had a refractive index, N$_D^{20°\,C.}$, measured by an Abbe refractometer, of 1.620 and an Abbe number of 33. Thus, it had good optical properties with a high refractive index and a high Abbe number.

EXAMPLE 5

A polymerization inhibitor, p-methoxyphenol (1.24 g; 0.01 mole), was added to a mixture of 78 g (1.0 mole) of 2-mercaptoethanol, 133 g (1.0 mole) of a 30 % aqueous solution of sodium hydroxide and 0.15 liter of methanol. While the mixture was cooled to below 10° C., 152 g (1.0 mole) of m-(chloromethyl)styrene was added dropwise over 3 hours. Then, the reaction mixture was continuously stirred for an additional 3 hours to complete the reaction. Water (1 liter) was added to the reaction mixture to separate it into an oil layer and an aqueous layer. The oil layer was washed with water and distilled under reduced pressure (140°-150 °C./1-2 mmHg) to give 105 g of 2-(3-vinylbenzylthio)ethanol as a colorless transparent liquid.

Purity determined by gas chromatography: 98.2 %

Elemental analysis values: C=68.1 %, H=7.25 %, S=16.4 %, O=8.25 % (calculated:: C=68.0 %, H=7.22 %, S=16.5 %, O=8.25 %)

Infrared absorption spectrum 3300 cm$^{-1}$ stretching vibration of —OH
3090 cm$^{-}$: stretching vibration of C—H of the benzene ring
2900–3000 cm$^{-1}$ stretching vibration of —CH$_2$—
1625cm$^{-}$: stretching vibration of CH$_2$=CH—
1500cm$^{-1}$ vibration of the benzene ring
1010cm$^{-1}$ stretching vibration of —O—

H$^1$-NMR spectrum 2.0 ppm: H of OH
2.6 ppm: H of CCH$_2$S
3.7 ppm: H of CCH$_2$O
3.75 ppm: H of CH$_2$ adjacent the benzene ring
5.5 ppm: H of =CH$_2$ of the vinyl group
6.6 ppm: H of —CH= of the vinyl group
7.2 ppm: H of the benzene ring

EXAMPLE 6

A mixture composed of 67 g of 2-(3-vinylbenzylthio)ethanol obtained in Example 5 and 33 g of m-xylylene diisocyanate was mixed uniformly with 0.2 g of Perbutyl O t-butylperoxy(2-ethylhexanoate)) and 50 ppm of dibutyltin was dilaurate as polymerization initiators. The mixture subjected to casting and polymerization under the same conditions as in Example 4. The resulting cured article was colorless and transparent and had a refractive index of N$_D^{20°\,C.}$ and an Abbe number of 33. It had lightweight with a specific gravity of 1.25 and good thermal resistance and impact strength.

EXAMPLES 7–9

In each run, each of the monomeric mixtures indicated in Table 1 was polymerized and cured using 0.5 g of Perbutyl O and 100 ppm of dibutyltin dilaurate as polymerization initiators in the same way as in Example 4. The cured articles obtained were colorless and transparent. The properties of these articles are shown in Table 1.

In the following table, the following abbreviations were used.

VBTE: 2-(3- and 4-vinylbenzylthio)ethanol mixture
MXDI: m-xylylene diisocyanate
TDI: tolylene diisocyanate
HMDI: hexamethylene diisocyanate

TABLE 1

| | Composition | | | Properties | | | | |
|---|---|---|---|---|---|---|---|---|
| Example | Aromatic compound | Isocyanate compound | Mole ratio of the vinyl group to the NCO group | Refractive index (N$_D^{20°\,C.}$) | Abbe number ($\nu_D^{20°\,C.}$) | Specific gravity | Thermal resistance | Impact strength |
| 7 | VBTE (69 g) | TDI (31 g) | 1.0 | 1.635 | 30 | 1.30 | good | good |
| 8 | VBTE (70 g) | HMDI (30 g) | 1.0 | 1.594 | 35 | 1.20 | good | good |
| 9 | VBTE (67 g) | MXDI (33 g) | 1.0 | 1.621 | 33 | 1.25 | good | good |

EXAMPLES 10–12

In each run, each of the monomeric mixtures indicated in Table 2 was polymerized and cured in the same way as in Examples 7-9.

The resulting cured articles were colorless and transparent. The properties of these articles are shown in Table 2.

The following additional abbreviations are used in Table 2.

St: styrene
DVB: divinylbenzene
IG: ethylene glycol dimethacrylate

TABLE 2

| | Composition | | | Properties | | | | |
|---|---|---|---|---|---|---|---|---|
| Example | Aromatic compound | Isocyanate compound | Other vinyl monomer | Refractive index (N$_D^{20°\,C.}$) | Abbe number ($\nu_D^{20°\,C.}$) | Specific gravity | Thermal resistance | Impact strength |
| 10 | VBTE (54 g) | MXDI (26 g) | St (20 g) | 1.615 | 32 | 1.21 | good | good |
| 11 | VBTE (54 g) | MXDI (26 g) | DVB (20 g) | 1.618 | 32 | 1.22 | good | good |
| 12 | VBTE (54 g) | MXDI (26 g) | IG (20 g) | 1.602 | 35 | 1.25 | good | good |

We claim:

1. A curable composition comprising at least one sulfur-containing aromatic vinyl compound represented by

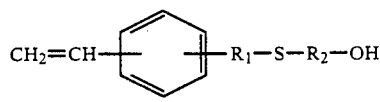

[I]

wherein R$_1$ represents an alkylene group having 1 to 3 carbon atoms and R$_2$ represents an alkylene group having 2 to 8 carbon atoms, and the two bonds in the benzene ring are meta or para to each other, an isocyanate compound and a radical polymerization initiator.

2. The curable composition according to claim 1 in which the ratio of the total moles of the vinyl group to the total moles of the isocyanate groups is in the range of from about 0.5 to about 2.

3. The curable composition of claim 1 which further comprises another radical polymerizable vinyl monomer.

4. The curable composition according to claim 3 in which the ratio of the total moles of the vinyl group to the total moles of the isocyanate groups is in the range of from about 0.5 to about 2.

5. The curable composition of claim 3 in which the weight ratio of the sulfur-containing aromatic vinyl compound and the isocyanate compound to the other radical polymerizable vinyl monomer is in the range from 100:0 to 60:40.

6. A crosslinked polymer article obtained by curing the curable composition of any one of claims 1 to 5 in a mold.

7. A lens composed of the crosslinked polymer article of claim 6.

8. A process for producing a crosslinked polymer article, which comprises
 (a) preparing a curable composition of any one of claims 1 to 5,
 (b) feeding the curable composition into a mold,
 (c) heating and curing the curable composition in the mold, and then
 (d) withdrawing the resulting crosslinked polymer composition from the mold.

9. The process of claim 8 in which the heating is carried out at a temperature of 40° to 130° C.

* * * * *